(12) United States Patent
Truckai et al.

(10) Patent No.: US 11,529,048 B2
(45) Date of Patent: Dec. 20, 2022

(54) ENDOSCOPE AND METHOD OF USE

(71) Applicant: Meditrina, Inc., San Jose, CA (US)

(72) Inventors: Csaba Truckai, Saratoga, CA (US); Britta Kotov, San Jose, CA (US); John H. Shadduck, Menlo Park, CA (US)

(73) Assignee: Meditrina, Inc., San Jose, CA (US)

( * ) Notice: Subject to any disclaimer, the term of this patent is extended or adjusted under 35 U.S.C. 154(b) by 0 days.

(21) Appl. No.: 17/648,800

(22) Filed: Jan. 24, 2022

(65) Prior Publication Data

US 2022/0142466 A1 May 12, 2022

Related U.S. Application Data

(63) Continuation of application No. 16/934,914, filed on Jul. 21, 2020, now Pat. No. 11,259,695.

(51) Int. Cl.
| | | |
|---|---|---|
| A61B 1/313 | (2006.01) | |
| A61B 1/05 | (2006.01) | |
| A61B 1/005 | (2006.01) | |
| A61B 1/00 | (2006.01) | |
| A61B 1/07 | (2006.01) | |
| A61B 1/06 | (2006.01) | |

(52) U.S. Cl.
CPC ........ *A61B 1/3132* (2013.01); *A61B 1/00009* (2013.01); *A61B 1/00045* (2013.01); *A61B 1/0052* (2013.01); *A61B 1/00119* (2013.01); *A61B 1/05* (2013.01); *A61B 1/0684* (2013.01); *A61B 1/07* (2013.01); *A61B 2562/0219* (2013.01); *A61B 2562/166* (2013.01)

(58) Field of Classification Search
CPC ....... A61B 1/05; A61B 1/051; A61B 1/00045; A61B 1/00183; A61B 1/018
See application file for complete search history.

(56) References Cited

U.S. PATENT DOCUMENTS

| | | | |
|---|---|---|---|
| 5,025,778 | A | 6/1991 | Silverstein et al. |
| 5,063,018 | A | 11/1991 | Fontirroche et al. |
| 5,166,787 | A | 11/1992 | Irion |
| 5,351,678 | A | 10/1994 | Clayton et al. |
| 5,882,346 | A | 3/1999 | Pomeranz et al. |
| 5,993,462 | A | 11/1999 | Pomeranz et al. |
| 6,997,896 | B2 | 2/2006 | Novak |
| 7,683,155 | B2 | 3/2010 | Inatomi et al. |
| 8,460,182 | B2 | 6/2013 | Ouyang et al. |
| 8,702,594 | B2 | 4/2014 | Edidin et al. |
| 9,033,870 | B2 | 5/2015 | Farr et al. |
| 9,468,367 | B2 | 10/2016 | Ouyang et al. |
| 9,913,570 | B2 | 3/2018 | Kucharski et al. |
| 10,433,717 | B1 | 10/2019 | Truckai et al. |
| 10,524,636 | B2 | 1/2020 | Ouyang et al. |
| 10,588,493 | B2 * | 3/2020 | Elia .............. A61B 1/00135 |
| 11,259,695 | B2 | 3/2022 | Truckai et al. |

(Continued)

FOREIGN PATENT DOCUMENTS

| | | |
|---|---|---|
| CN | 101972169 | 1/2016 |
| WO | WO 2017/216835 | 12/2017 |
| WO | WO 2019/178180 | 9/2019 |

*Primary Examiner* — Alexandra L Newton
(74) *Attorney, Agent, or Firm* — Levine Bagade Han LLP (57) ABSTRACT

Endoscopes and methods of their use, where the endoscopes provide a low profile or cross-section which facilitates introduction through small body passages, such as patient's cervix, and into body cavities, such a patient's uterus.

16 Claims, 8 Drawing Sheets

(56) References Cited

U.S. PATENT DOCUMENTS

| | | |
|---|---|---|
| 2003/0208192 A1 | 11/2003 | Truckai et al. |
| 2003/0212427 A1 | 11/2003 | Truckai et al. |
| 2004/0247849 A1 | 12/2004 | Truckai |
| 2005/0272975 A1 | 12/2005 | Mcweeney et al. |
| 2006/0241276 A1 | 10/2006 | Inatomi et al. |
| 2007/0213749 A1 | 9/2007 | Kogasaka et al. |
| 2009/0149878 A1 | 6/2009 | Truckai et al. |
| 2010/0211076 A1 | 8/2010 | Germain et al. |
| 2011/0004157 A1 | 1/2011 | Dewaele et al. |
| 2011/0184233 A1 | 7/2011 | Fructus et al. |
| 2011/0251615 A1 | 10/2011 | Truckai et al. |
| 2011/0295262 A1 | 12/2011 | Germain et al. |
| 2012/0065469 A1* | 3/2012 | Allyn .................. A61B 1/0684 600/109 |
| 2012/0245416 A1 | 9/2012 | Viola |
| 2013/0046137 A1 | 2/2013 | Zhao et al. |
| 2013/0102846 A1 | 4/2013 | Sjostrom et al. |
| 2013/0172676 A1 | 7/2013 | Levy et al. |
| 2013/0190562 A1 | 7/2013 | Smith et al. |
| 2014/0046305 A1 | 2/2014 | Castro et al. |
| 2014/0303611 A1 | 10/2014 | Shadduck et al. |
| 2014/0375784 A1 | 12/2014 | Massetti |
| 2015/0066033 A1 | 3/2015 | Jorgensen |
| 2016/0022470 A1 | 1/2016 | Gillis et al. |
| 2016/0346037 A1 | 12/2016 | Truckai et al. |
| 2017/0035277 A1 | 2/2017 | Kucharski et al. |
| 2017/0265879 A1 | 9/2017 | Washburn et al. |
| 2017/0319047 A1 | 11/2017 | Poulsen et al. |
| 2018/0084971 A1 | 3/2018 | Truckai et al. |
| 2018/0160893 A1* | 6/2018 | Truckai .................. A61B 1/307 |
| 2018/0206712 A1* | 7/2018 | Begg .................... A61B 1/018 |
| 2019/0099062 A1 | 4/2019 | Ishihara et al. |
| 2019/0104932 A1 | 4/2019 | Truckai et al. |
| 2019/0282073 A1 | 9/2019 | Truckai |
| 2019/0321077 A1* | 10/2019 | Kienzle .................. A61B 1/042 |
| 2019/0343370 A1 | 11/2019 | Kumagai et al. |
| 2020/0000326 A1 | 1/2020 | Truckai et al. |
| 2020/0060526 A1 | 2/2020 | Toth et al. |
| 2020/0187751 A1* | 6/2020 | Zheng .................. A61B 1/0008 |
| 2022/0022740 A1 | 1/2022 | Truckai et al. |

* cited by examiner

ENDOSCOPE AND METHOD OF USE

CROSS-REFERENCE TO RELATED APPLICATIONS

This application is a continuation of U.S. patent application Ser. No. 16/934,914 filed Jul. 21, 2020, the content of which is incorporated herein by reference in its entirety.

BACKGROUND OF THE INVENTION

1. Field of the Invention

The present invention relates to an endoscope assembly, and more particularly to an endoscope with a working channel for use in hysteroscopy, and a method of use of the endoscope assembly.

Endoscopes are used in a wide variety of minimally invasive surgical procedures, including laparoscopy, arthroscopy, and the like. Of particular interest to the present application, hysteroscopy is a minimally invasive procedure for resecting fibroids and performing similar interventions in a patient's uterus. Hysteroscopy utilizes a hysteroscope which is a type of endoscope that carries optics for viewing, a light source for illumination, and a working channel. Interventional tools, such as a resecting device, an electrosurgical cautery device, forceps, and the like, can be introduced though the working channel of the hysteroscope to perform a therapeutic procedure while the patient's uterus is distended with a fluid media. The hysteroscope is often introduced through a passage in a transcervical sheath which also allows for fluid inflows and outflows into and out of the uterine cavity.

Heretofore, to accommodate the optics, light sources, and the working channel, hysteroscopes have had large diameters which require passage of a large sheath through the cervix, further requiring dilation of the cervix prior to insertion. Cervical dilation requires stretching the cervix with a series of dilators of increasing diameter and can be traumatic for many patients.

For these reasons, it would be desire able to provide hysteroscopes having relatively small diameters to reduce or eliminate the need to dilate the patient's cervix prior to introduction of the hysteroscope. It would be further desirable to provide methods utilizing such hysteroscopes, and still further desirable to provide similar designs and methods for all types of endoscopes used in a variety of minimally invasive procedures including, laparoscopy, arthroscopy, and the like. At least some of these objectives will be met by the inventions described and claimed hereinafter.

SUMMARY OF THE INVENTION

The present invention provides an endoscope and a method for using the endoscope in hysteroscopies and other endoscopic surgical procedures. The endoscope design of the present invention provides a low profile or cross-section which facilitates introduction through small body passages, such as patient's cervix, and into body cavities, such a patient's uterus. Particular endoscope designs incorporate a number of features which can be used alone or in combination to achieve the certain objectives of the present invention, such as a reduced endoscope shaft diameter and reduced patient trauma during introduction of the endoscope.

In one variation, the device can comprise an endoscope device (either a stand-alone endoscopic system or an endoscopic device that is configured to be joined with a handle or other equipment to complete the endoscopic system for use with a tool. The endoscopic device or device can be configured for coupling with other endoscopic tools to complete an endoscopic system for use in a medical procedure. Alternatively, an endoscopic device or device can be used as a stand-alone system for a medical procedure.

In one variation, an endoscopic device can include an elongated shaft having an open distal end and an open passageway extending therethrough; a sensor assembly comprising an image sensor having an optical axis that is perpendicular to the image sensor and a field of view that is angled relative to the optical axis, the sensor assembly sized to fit within the open distal end; a flex circuit coupled to the sensor assembly and extending proximally within the open passageway; a flexible arm structure having a first end coupled to the sensor assembly and a second end within the open passageway and affixed to a base structure such that the elongated shaft is moveable relative to the base structure, the flexible arm structure, and the sensor assembly; wherein the flexible arm structure comprises an insertion position when restrained within the elongated shaft such that the flexible arm structure positions the sensor assembly so the optical axis is angled relative to a shaft axis of the elongated shaft; and wherein the flexible arm structure biases towards a deployed position when unrestrained by the elongated shaft such that the flexible arm structure positions the sensor assembly away from the shaft axis of the elongated shaft, wherein as the flexible arm structure moves through the open distal end of the elongated shaft the sensor assembly can be moved between the insertion position and the deployed position such that the field of view is oriented to observe the tool advanced through the open distal end of the elongated shaft. As noted herein, the endoscopic device of claim can further include a handle where the flex circuit extends into the handle.

The endoscope devices and components described herein can optionally include an illumination source such as a fiber, LED, or other source of illumination that provides visible light or other wavelengths of electromagnetic radiation whether visible or not. The illumination source can be positioned towards the open distal end. In additional variations, the illumination source is coupled to the sensor assembly. Alternatively, or in combination, the illumination source is coupled to the elongated shaft.

In additional variations, the endoscopic device can further include a working channel extending in the open passage, the working channel having a wall such that the open passageway external to the working channel forms a fluid channel. Such a working channel can be formed from a second tube that is positioned within the elongated shaft. Alternatively, or in combination, the elongated shaft can include one or more separators that allow for fluid isolation of the open passageway of the shaft and the working channel. In any case, a portion of any structure that forms the working channel can form the base structure, which will permit relative movement of the elongated shaft to the base structure, flexible circuit and flexible arm structure.

The devices described herein can be configured so that the working channel is configured to be coupled to a negative pressure source. In additional variations, the devices can include a fluid source in communication with the flow channel and configured to provide fluid inflows from the open distal end. Variations of the devices include a flow channel has a reduce cross-sectional area through a distal portion of the elongated shaft when in the insertion position and a greater cross-sectional area in the deployed position.

The devices of the present invention can further include one or more accelerometers coupled to the sensor assembly and/or the elongated shaft. In one variation, an accelerometer is positioned proximal to the image sensor on the flex circuit.

The image sensor of the devices disclosed herein can be configured to send image signals to an image processor and any accelerometer can be configured to send position signals to the image processor, wherein the processor includes algorithms for displaying images on a display in a selected orientation in any rotational position of the inner sleeve and the image sensor.

Variations of the device can include multiple illumination sources. For example, a variation of a device includes at least a first illumination source and a second illumination source, each respectively positioned on a first arm and a second arm of a distal end of the flex circuit.

The devices described herein can use the elongated shaft to deflect and position the image sensor. For example, the elongated shaft can be configured to contact a first deflecting surface, where relative movement between the deflecting surface and the elongated shaft moves move the flexible arm structure between the insertion position and the deployed position. Variations of the devices can include flexible arm structures that have a living hinge portion and the deflecting surface is distal to the living hinge portion. In additional variations, the flexible structure can be tensioned in the first position. The first deflecting surface can comprise an angled portion of the flexible arm structure that is non-flexible. In an additional variation, the first deflecting surface comprises a ramp portion coupled to the sensor assembly. Any of the devices described herein can also include a flexible arm structure that further comprises a second deflecting surface configured to displace upon advancement of the tool against the second deflecting surface.

The present disclosure also includes endoscopic methods of treating or examining a patient. For example, such a method can include providing a system including an endoscope, image processor, controller and inflow and outflow pumps, where the endoscope has an axially-extending shaft with a distal spring structure carrying an image sensor, where the spring structure is moveable between (i) a first configuration with a reduced profile where the sensor's field of view is oriented to observe introduction of the shaft through a passage in the patient's body, and (ii) at least one second configuration having an expanded profile with the image sensor moved away from the a shaft axis where the field of view is oriented to observe a tool introduced through a working channel therein; introducing the shaft in the first configuration through a body passageway into a working space while viewing images from the image sensor; operating the inflow and outflow pumps with the controller to circulate fluid flows into the patient's body; moving the spring structure from the first configuration to the second configuration such that an optical axis of the image sensor intersects with the shaft axis; advancing a tool through a working channel into the working space; and viewing the tool with images from the image sensor and performing a treatment in the working space with the tool.

Additional variations of the method can include the use of an endoscope that carries an accelerometer configured to send position signals to the controller and image processor, further comprising the step of operating the controller and image processor to continuously adjust images to an upright orientation.

In another variation, the method can further include operating the inflow and outflow pumps to circulate fluid flows while maintaining a selected pressure in the working space.

A variation of the method includes sliding an outer sleeve of the shaft relative to an inner sleeve of the shaft wherein the outer sleeve slidably contacts a deflecting surface on the spring structure to move the spring structure between the first configuration to the second configuration.

Another variation of the method includes advancing a tool through a working channel of shaft and the tool contacts a deflecting surface on the spring structure to move the spring structure between the first configuration to the second configuration.

In a first aspect, an endoscope constructed in accordance with the principles of the present invention comprises handle coupled to a shaft having a diameter and extending about a longitudinal axis to a working end. The shaft includes an outer sleeve that is axially moveable relative to an inner sleeve, and an image sensor is carried by a flexible spring-type member attached to a distal end of the inner sleeve. The flexible member has at least one living hinge portion and often has two living hinge portions which can be actuated between tensioned and repose positions. The image sensor is typically rectangular and has a diagonal dimension measured from a first corner to a second diagonally opposed corner. The outer sleeve of the shaft is typically cylindrical and has a diameter. The inner sleeve has a working channel therein which extends through handle and the shaft open termination in a distal end of the shaft. The outer sleeve can be moved from a first distal position to a second proximal position relative to the inner sleeve and working channel therein. Such movement of the outer sleeve to positions the image sensor distally from the bore of the outer sleeve and allows the spring force inherent in a living hinge portion of the flexible member and move the image sensors away from the longitudinal axis of the shaft. When the working end is moved from the first insertion position to the second deployed position, the space within the outer sleeve beyond the distal end of the inner sleeve, which comprises a distal portion of the overall working channel, increases in cross-section to accommodate a tool as it is introduced through a endoscope. In accordance with the present invention, a combination or sum of (1) the diagonal dimension of the image sensor and (2) a diameter of the working channel is greater than a diameter dimension of the shaft. These relative dimensions can maximize the cross-section of the working channel through the endoscope in the deployed position while minimizing the diameter of the shaft in the insertion position for introducing the shaft though a body passage into a working space in a patient.

In specific examples of this endoscope, the ratio of the diagonal dimension of the image sensor to the shaft diameter is at least 0.5:1 and often the ratio is greater than 0.6:1. In still other specific examples, the ratio of the working channel cross-section to the shaft diameter is at least 0.5:1 and often the ratio is greater than 0.6:1.

In still further specific examples, the image sensor is carried in a generally transverse or orthogonal orientation relative to the shaft's longitudinal axis with a distal-facing optical axis and field of view. The optical axis is adjusted when the working end is moved from the insertion position to the deployed position. In one example, the optical axis of the image sensor may change as an interventional tool is introduced through the working channel, wherein the tool abuts and deflects the flexible member to assist in moving the image sensor away from the longitudinal axis of the shaft. In another specific example, movement of the outer sleeve distally while a tool shaft extends through the working channel can be used to actuate a second living hinge portion of the flexible member to alter or adjust the optical axis and field of view of the image sensor.

In another aspect of the present invention, the single-use endoscope includes an image sensor, two LEDS, and at least one accelerometer mounted on a single flex circuit that extends through the endoscope from a cable that is configured with a connector at a proximal end thereof. The use of such a single flex circuit eliminates the need for a circuit board and connection in the handle which make the device economical. Further, the flux circuit has electrically insulated layers exposed on all surfaces which are capable of shielding the electrical leads of the image sensor and accelerometer from any possible electrical interference, including any interference from an electrosurgical tool used with the endoscope.

In another aspect of the present invention, a method for imaging and treating a body cavity comprises providing an endoscope having any of the features and combinations of features described above, for example, including an elongated member extending about a central or longitudinal axis through a handle, proximal shaft portion and a distal shaft portion, an image sensor carried by the distal shaft portion, and a working channel extending through the handle and shaft. The endoscope is advanced through a body passage in a first reduced-diameter configuration using the image sensor. Thereafter, a working space in a body cavity is imaged using the image sensor and the image sensor is actuated to move away from, or diverged from, the axis of the endoscope shaft. A tool may then be advanced through the working channel of the endoscope into the body cavity. The tool may then be used to treat the body cavity while the tool and the image sensor remain diverged relative to each other.

BRIEF DESCRIPTION OF THE DRAWINGS

Additional aspects of the invention will become clear from the following description of illustrative embodiments and from the attached drawings, in which.

DETAILED DESCRIPTION OF THE INVENTION

Figure 1:
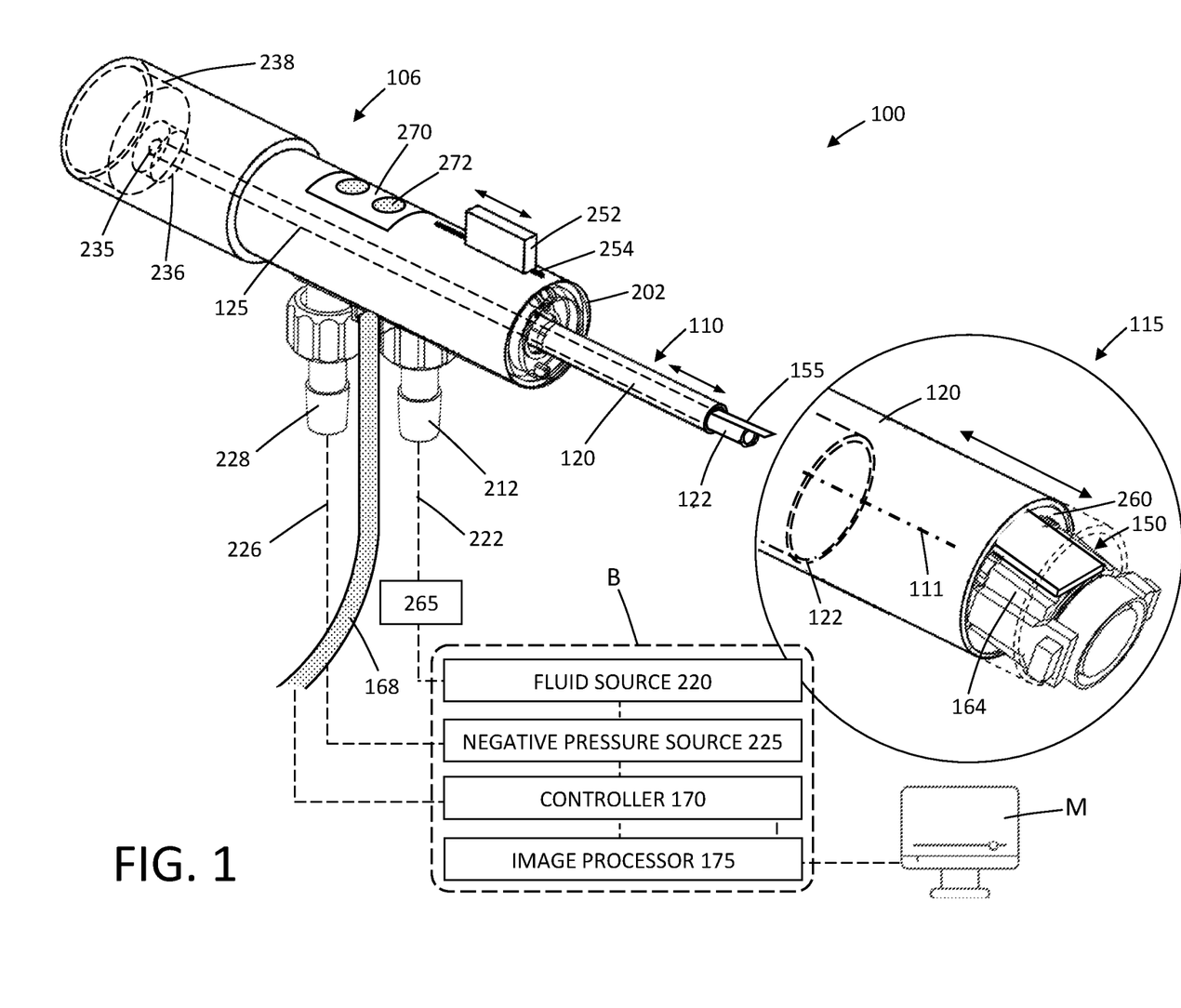
FIG. 1 is a perspective view of an embodiment of an endoscope corresponding to the invention, with an enlarged view of the distal working end.
Figure 2:
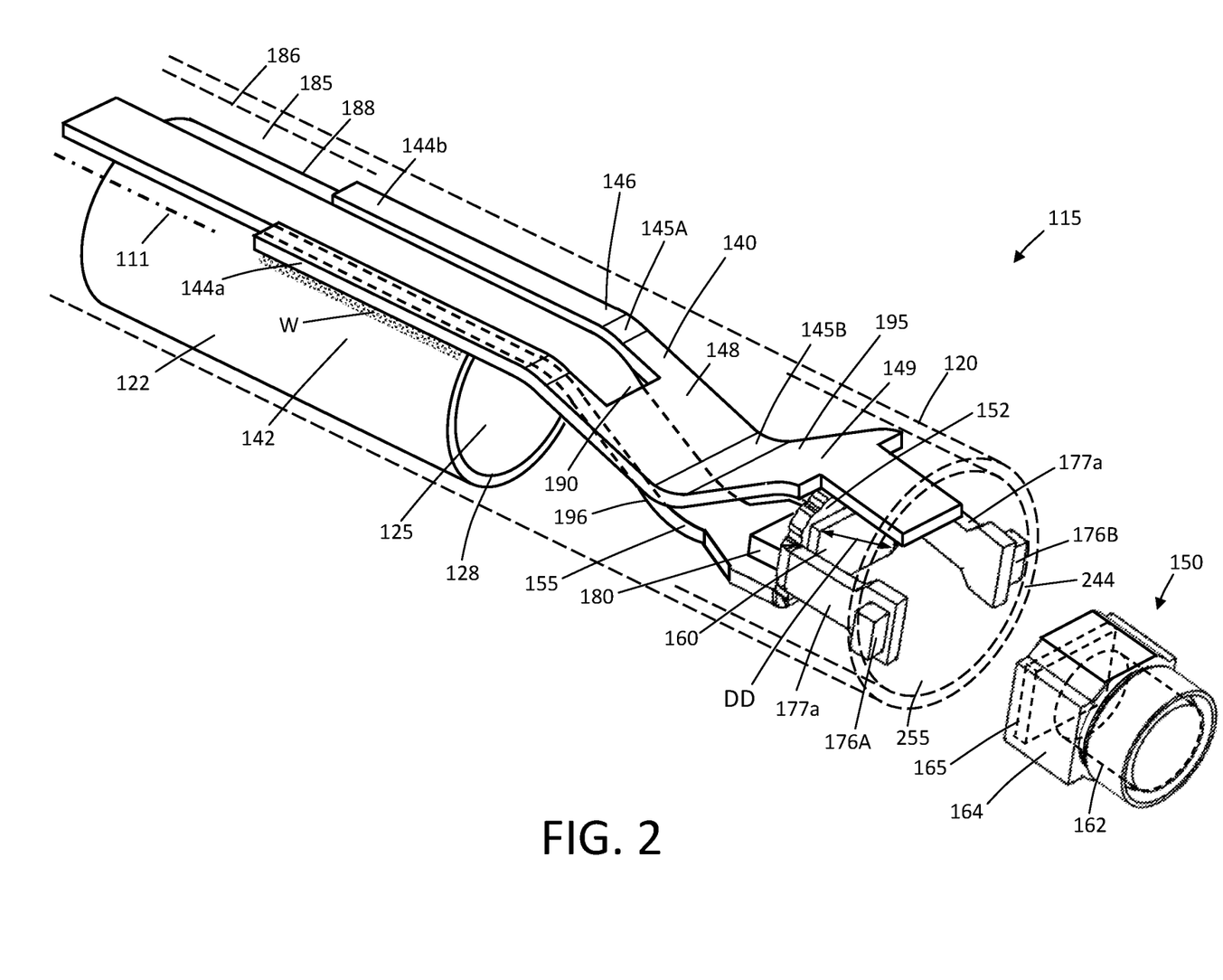
FIG. 2 is a perspective view of the an inner sleeve of the endoscope shaft together with an assembly of a flexible member and flex circuit that extend distally from the inner sleeve and carry the image sensor, an accelerometer, and LEDs, where the flexible member has first and second living hinge portions, and where the outer sleeve is shown with a broken line.

FIG. 1 illustrates an endoscope 100 corresponding to the invention which includes a proximal handle 106 coupled to a shaft or shaft assembly 110 extending about longitudinal axis 111 to a distal working end 115. Referring to FIGS. 1 and 2, the shaft includes an outer sleeve 120 and an inner sleeve 122 having a passageway or working channel 125 therein that extends though the handle 106 and inner sleeve 122 to a distal open end 128. In one variation, the shaft 110 has a diameter ranging between 2.5 mm and 10 mm with a length configured for use in hysteroscopy. More commonly, the shaft diameter is from 3 mm to 6 mm in diameter. The working channel 125 or tool-receiving channel is adapted for receiving various types of tools and typically has a diameter ranging between 1 mm and 6 mm, and more often from 2 mm to 4 mm. In use, a tool used in the endoscope can have a straight shaft and comprise a biopsy device, an electrocautery device, an electrosurgical ablation device, a resection device or any other type of tool known in the art. Typically, the endoscope 100 of FIG. 1 configured for single-use and is not intended for sterilization and re-use.

Referring to FIG. 2, the working end 115 includes a flexible spring structure or member 140 which functions as a leaf spring and is coupled to the distal end 142 of inner sleeve 122, for example, by welding a proximal portion of the flexible member 140 to the distal end 142 of inner sleeve 122. In one variation shown in FIG. 2, the flexible member 140 has proximal leg portions 144a and 144b that are welded to inner sleeve 122 along weld lines W. Alternatively, the flexible member 140 can consist of a machined portion of the inner sleeve 122. As will be described further below, the flexible member 140 as shown in FIG. 2 and FIGS. 4A-4C is configured with first and second living hinge portions 145A and 145B, each with an inherent sprint force, that are adapted to flex independently to provide a plurality of selected flexed positions. It can be seen that the flexible member 140 has a proximal portion 146 that is proximal to living hinge 145A, an intermediate portion 148 between living hinges 145A and 145B and a distal portion 149 that is distal to the second living hinge 145B.

As can be seen in FIGS. 1 and 2, an image sensor 150 is coupled to a distal end portion 152 of a flex circuit 155 that extends through the shaft 110 and is adjacent the flexible member 140 in the working end 115 (FIG. 2). The term image sensor 150 as used herein refers to the assembly of a CMOS sensor chip 160, a lens 162 (consisting of an assembly of optical elements) and a sensor housing 164 as can be seen in FIGS. 1 and 2. In the partially exploded view of FIG. 2, the CMOS sensor chip 160 is shown coupled to flex circuit 155 where the recess 165 in the sensor housing 164 is dimensioned to receive the sensor chip 160. In a variation, the sensor chip 160 is an OmniVision part number OV9734 CMOS '720p HD PurCel® image sensor available from OmniVision Technologies, Inc., 4275 Burton Drive, Santa Clara Calif. 95054. This sensor chip 160 has a field of view FOV of 100o about an optical or view axis A.

The sensor chip 160 is coupled through cable 168 to an image processor 170 and a controller 175 by electrical leads in the flex circuit 155 that extends through the shaft 110 and handle 106 to the cable 168. The controller 175 is adapted to control operating parameters of the sensor chip 160 as well as other components of the endoscope 100 as will be described below. The controller 175 and image processor 170 are typically housed in a console or base unit B (FIG. 1). A video display or monitor M is also connected to the image processor 170 and controller 175 for viewing images from the image sensor 150 (FIG. 1).

As can be seen in FIGS. 1 and 2, the flex circuit 155 and sensor housing 164 also carry one or more light emitters, for example, two LEDs indicated at 176A and 176B. Electrical leads in the flex circuit 155 connect the LEDs 176A-176B to the controller 175 which includes an electrical source to provide power to the LEDs. In FIG. 2, it can be seen that LEDs 176A and 176B are connected to two opposing arms 177a and 177b of the flex circuit 155. The flex circuit 155 and its arms 177a and 177b are designed with weakened thickness sections across the flex circuit that allows 90o bends of the angled distal end portion 152 that couples to the sensor chip 160 and the arms 177a and 177b. The angled distal flex circuit portion 152 and the arms 177a and 177b are bonded to the sensor housing 164 to be maintained in the configuration shown in FIG. 1.

Figures 4A, 4B, 4C:
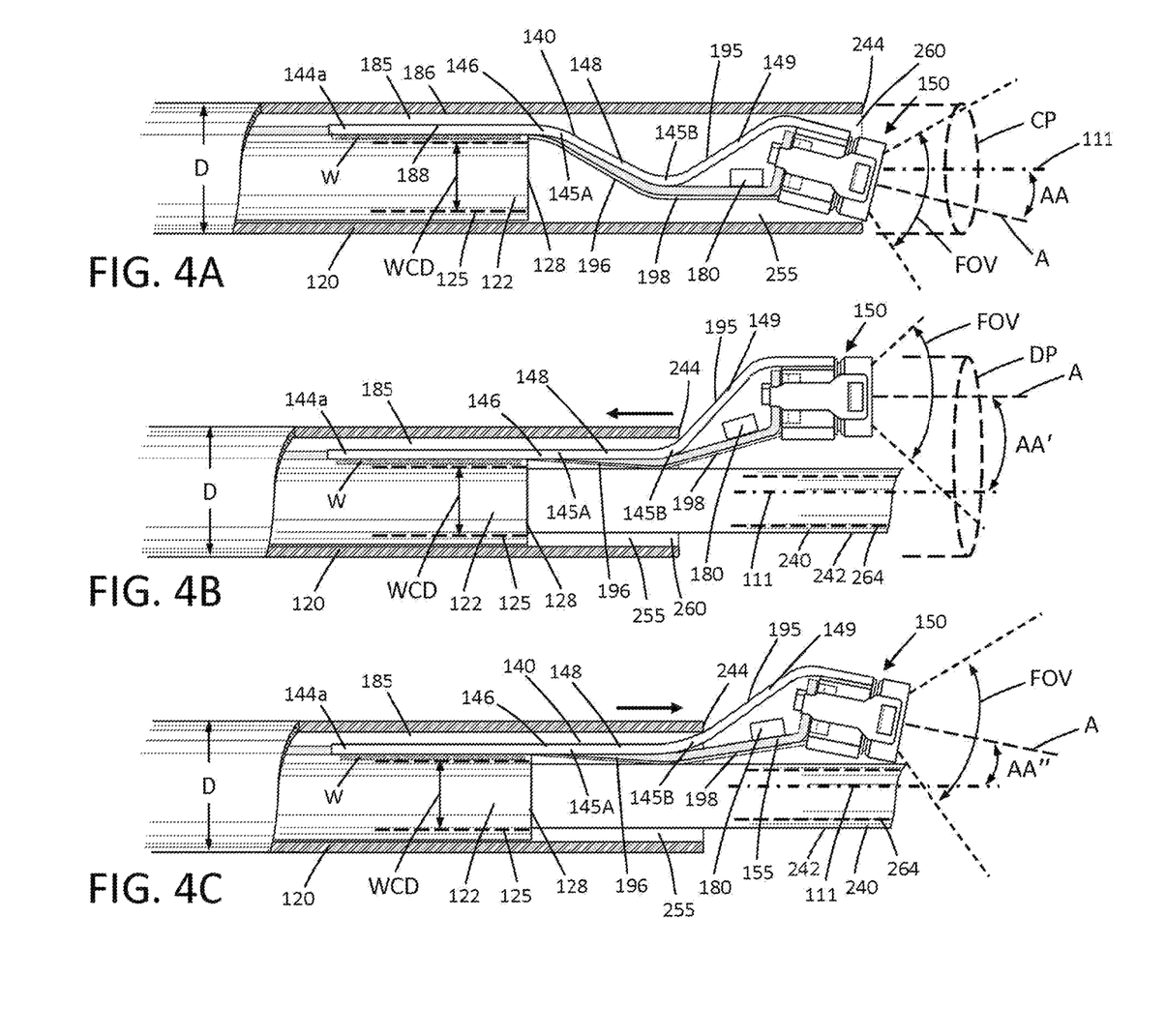
FIG. 4A is a view of a distal portion of the endoscope shaft in a first, straight insertion configuration with an outer sleeve in cut-away part-sectional view, and an inner sleeve, flexible member, flex circuit, accelerometer, LEDS and image sensor in elevational view, wherein the flexible member, flex circuit and image sensor are in a first position within a cylindrical profile or envelope defined by the outer sleeve of the shaft, and wherein such an insertion configuration is adapted for insertion through body passageway to a treatment site in a patient's body, for example, a patient's cervical canal that opens to a uterine cavity.
FIG. 4B is a cut-away and sectional view of the endoscope shaft of FIG. 4A in a second, non-straight configuration wherein the flexible member, flex circuit and image sensor are in a second position that is moved outwardly by the spring force of the first living hinge portion and away from the cylindrical envelope defined by the outer sleeve, where such a second position provides a large cross-section working channel to receive a straight shaft of a treatment tool.
FIG. 4C is a cut-away and sectional view of the endoscope shaft of FIGS. 4A-4B in a third, non-straight configuration wherein the flexible member is deflected by distal sliding of the outer sleeve which overcomes the spring force inherent in the second living hinge portion, and where the orientation of the image sensor can be adjusted to a selected angle toward the longitudinal axis of the shaft.

In FIGS. 2 and 4A, it can be seen that the flex circuit 155 also carries an accelerometer 180 with electrical leads in the flex circuit 155 connected to the controller 175 and image processor 170 (FIG. 1). The accelerometer 180 sends signals to the controller 175 and image processor 170 regarding movement and orientation of the working end 115 wherein such signals are processed by control algorithms to adjust the image on the video display or monitor M (FIG. 1) to be maintained in a selected orientation, such as an image-upright orientation, no matter how the endoscope 100 and working end 115 are rotated. As used herein, the term accelerometer is intended include any suitable accelerometer and/or gyroscope known in the art, and in one variation is an STMicro IIS2DH three-axis linear accelerometer, and in other variations can be any 3-axis accelerometer or 6 axis IMU (Inertial Motion Unit) with a 3 accelerometer axes and 3 gyroscope axes, e.g., an STMicro ISM330DLC, available from STMicroelectronics Inc., 7033 E. Greenway Parkway, Suite 300, Scottsdale,85254, Ariz.

Referring again to FIGS. 2, 3 and 4A, it can be seen that the flex circuit 155 extends through the shaft 110 in a space or inflow channel 185 between the inner surface 186 of outer sleeve 120 and the outer surface 188 of the inner sleeve 122. In one variation best seen in FIG. 2, as well as in FIGS. 4A-4C, the flex circuit 155 is configured to pass through a gap 190 between proximal leg portions 144a and 144b of the flexible member 140 such that a superior surface of the flexible member 140 is configured with a first deflecting surface or cam surface 195 which may be used to actuate the flexible member 140 as described below. In FIGS. 4A-4C, it can be seen that a second ramp or second cam surface 196 is provided on the inferior side of flex circuit 155 which also can also be used to actuate the flexible member 140. The second deflecting surface or cam surface 196 can consist of a durable, integrated outer layer 198 of the flex circuit 155 or can be a metal or polymer element connected to the flex circuit 155 (see FIGS. 4A-4B).

Figure 3:
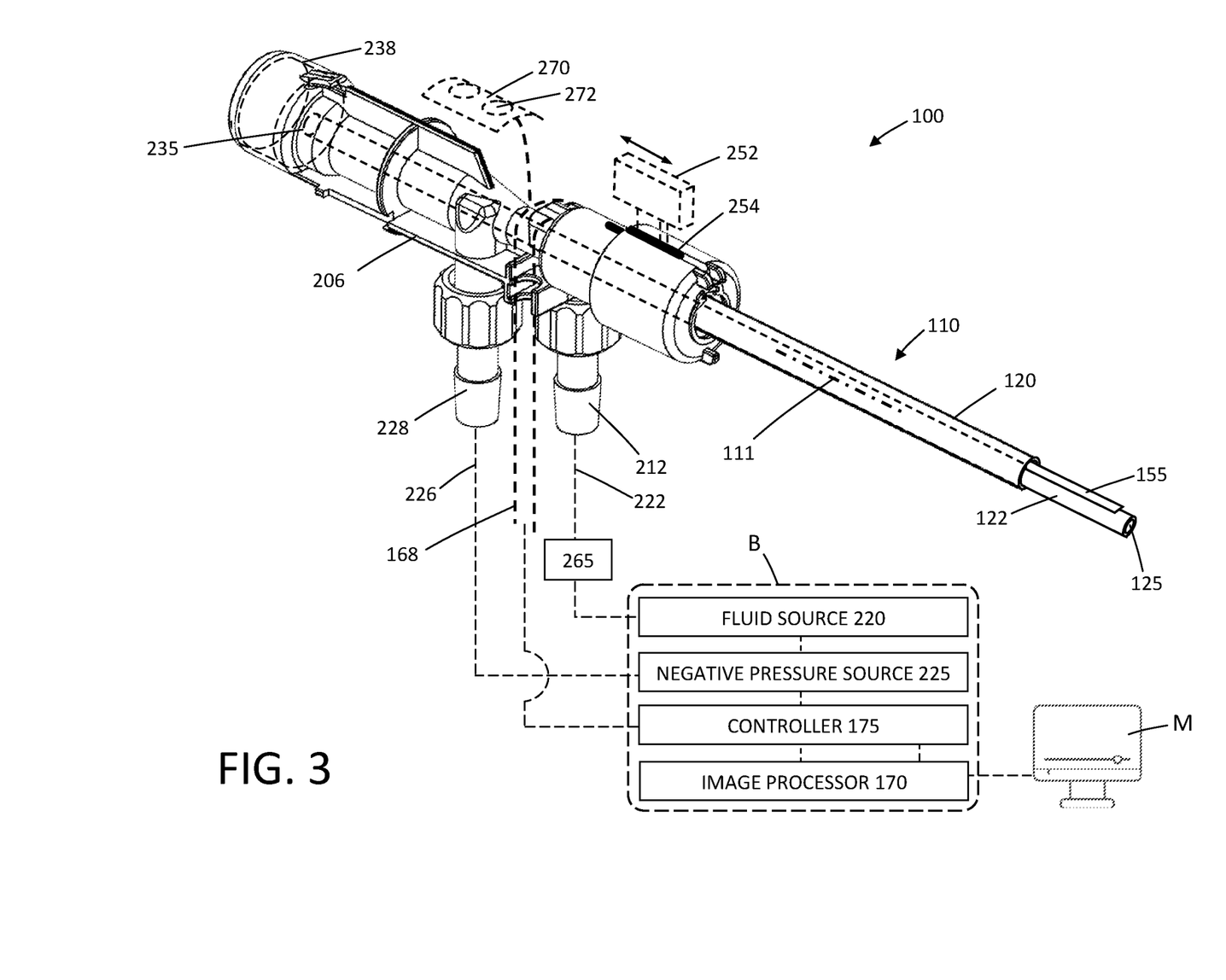
FIG. 3 is a perspective view of the handle portion of the endoscope of FIG. 1 with the outer shell removed to show the interior components thereof.

Referring now to FIG. 3, the handle 106 is shown with an outer shell 202 removed to better view the interior core 206 of the handle 106. It can be seen in a first Luer fitting 212 is formed as part of the core 206 and is in fluid communication with inflow channel 185 as described above between outer sleeve 120 and inner sleeve 122 extending through the shaft 110. A fluid source 220 can be connected to the Luer fitting 212 with inflow tubing 222 to provide fluid inflows to the inflow channel 185 (see FIG. 2). The fluid source 220 can be a gravity-flow bag or a fluid reservoir that is connected to an inflow pump as described below.

Still referring to FIG. 3, a negative pressure source (or outflow pump) 225 is connected to outflow tubing 226 which connects to a second Luer connector 228 formed in the core 206 of the handle 106 that further communicates with the working channel 125 or bore of the inner sleeve 122. In FIGS. 1 and 2, it can be seen that the working channel 125 in the inner sleeve 122 extends through the core 206 of the handle 106 to a proximal opening 235 and a seal 236 in a recess 238 in the proximal end of handle 106. The seal 236 can comprise any type of elastomeric seal know in the art, such as a duckbill valve or the like, to accommodate the shaft 240 of a tool 242 inserted through working channel 125 to prevent fluid leakage through proximal opening 235.

Now turning to FIGS. 4A-4C, it can be seen how the flexible member 140 and image sensor 150 can be moved from a first position as shown in FIG. 4A to a second position as shown in FIG. 4B and to a range of third positions as shown in FIG. 4C. As can be easily understood, the working end 115 in the first position of FIG. 4A defines a cylindrical profile CP or envelope that consists of the outer diameter D of the outer sleeve 120. This cylindrical insertion profile CP has a lesser cross-section and is adapted for atraumatic insertion of the shaft 110 through a body passageway into a body cavity, such as inserting the device through a patient's cervical canal into a uterine cavity. In this cylindrical insertion profile CP, the image sensor 160 and lens 162 have an optical axis A and field of view FOV that are angled relative to the longitudinal axis 111 of the shaft 110 such that the field of view FOV allows visualization of the body passageway as the working end 115 is advanced through such a body passageway. The optical axis A typically may be angled from 10° to 40° away from the longitudinal axis 111 (indicated at AA) of the shaft 110 in the first position of FIG. 4A.

FIG. 4B shows the outer sleeve 120 moved in the proximal direction relative to inner sleeve 122 wherein the flexible member 140 and the image sensor 160 are moved to a second deployed position in which the image sensor 160 is moved outwardly and away from the longitudinal axis 111 of the shaft 110. As can be understood from FIG. 4B, the distal edge 244 of the outer sleeve 120 slides proximally against the first deflecting surface 195 of the superior side of flexible member 140 and the spring force of living hinge portion 145A of the flexible member 140 is biased to move from the position of FIG. 4A to the position of FIG. 4B. Typically, the flexible member 140 is tensioned in the first position of FIG. 4A and non-tensioned in the position of FIG. 4B. Optionally, or in addition, the spring force of living hinge portion 145A may be configured such that the tool 242 introduced through the working channel 125 (broken line in FIG. 2A) contacts the second deflecting surface 196 on the flexible member 140 to deflect the living hinge portion 145A of flexible member 140 to the position shown in FIG. 4B. In other words, the living hinge portion 145A can be actuated from the position of FIG. 4A to the position of FIG. 4B entirely, or partially, by the spring force inherent in the living hinge portion 145A of the flexible member 140.

In FIG. 4B, the non-cylindrical deployed profile DP of the distal end 115 has a substantially greater cross-section than diameter D of the shaft 110. The configuration of FIG. 4B moves the image sensor 150 to a position where the field of view FOV is angled to observe the distal end of tool 242 introduced through the working channel 125 into the body cavity. In the deployed position of FIG. 4B, the optical axis A typically may be angled from 0° to 30° away from the longitudinal axis 111 of the shaft 110 (see AA").

FIG. 4C next show the outer sleeve 120 moved in the distal direction relative to inner sleeve 122 while the tool shaft 240 remains deployed through the working channel 125. As can be easily understood, the first living hinge 145A and proximal and intermediate portions 146, 148 of flexible member 140 are locked or constrained in the position of FIG. 4B, and distal movement of the distal edge 244 of outer sleeve 120 against the first deflecting surface 195 overcomes the spring force inherent in living hinge portion 145B to deflect the distal portion 149 of the flexible member 140 toward the axis 111 of the shaft 110. It can be understood that a range of deployed third positions are possible with one angled position shown in FIG. 4C, where the optical axis A typically may be moved to a selected angle ranging from 10° to 45° away from the longitudinal axis 111 of the shaft 110 (see AA"). Thus, the axial movement of the outer sleeve 120 can move the flexible member 140 from the non-tensioned position of FIG. 4B to a range of tensioned positions between the positions of FIGS. 4B and 4C.

Referring again to FIG. 4C, to return the working end 115 of the endoscope 110 to the insertion or cylindrical profile CP of FIG. 4A, the tool 242 is withdrawn from the working channel and 125 and the outer sleeve 120 is moved in the distal direction relative to inner sleeve 122.

In the variation shown in FIG. 1 and FIGS. 4A-4C, it can be understood that the outer sleeve 120 is moved proximally and distally relative to the inner sleeve 122 by finger grip 252 in the handle 106 that is moved axially in slot 254. It should be appreciated that relative movement of the inner and outer sleeves 120 and 122 can be accomplished either by sliding the outer sleeve 120 in the axially, or by sliding the inner sleeve 122 and flexible member 140 in an axial direction.

Figure 5:
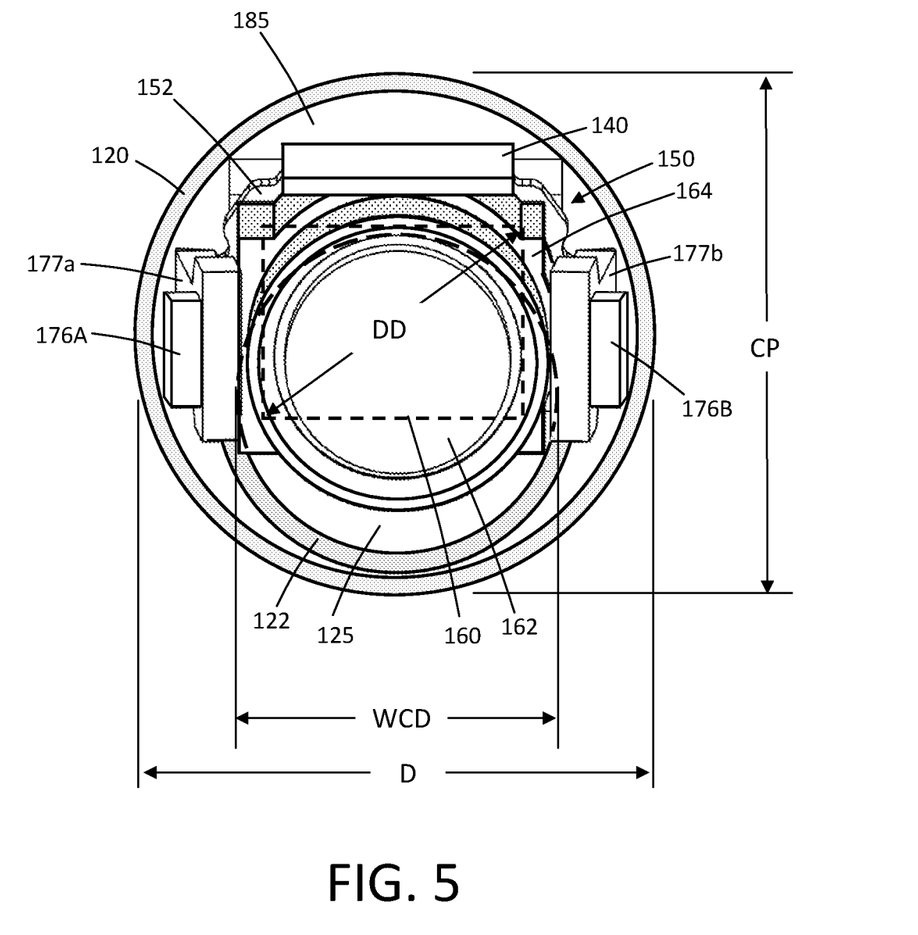
FIG. 5 is an end view of the shaft of the endoscope of FIGS. 1 and 2 showing the insertion profile of the endoscope as well as the diagonal dimension of the image sensor chip and the diameter of the working channel relative to the cylindrical insertion profile.

Referring now to FIGS. 3 and 4A-4C, it can be seen that inflow channel 185 extends through the shaft 110 and has an distal open termination 260 in the shaft 110 in the first position of FIG. 4A with the cylindrical insertion profile CP of the working end 115. The inflow channel 185 is used for fluid inflows during insertion of the working end 115 through a body passageway where the fluid inflow can distend and open the body passageway as well as provide fluid flows around the sensor lens 162 to maintain a clear field of view. Referring to FIG. 5, the cross-section of space 185 around the image sensor 150 is shown which provides the fluid inflow pathway in the first position of FIG. 4A. As can be understood from FIGS. 4B and 5, the inflow channel 185 remains open in the second position or deployed profile of the working end 115.

In one variation, the controller 170 includes fluid management algorithms that operate an inflow pump 265 connected to the inflow tubing 222 and inflow channel 185 together with an the negative pressure source (outflow pump) 225 coupled to outflow tubing 226 and the working channel 125 to provide fluid outflows which then can create a circulating flow through a patient's body passageway or body cavity, for example, a patient's cervical canal and uterine cavity. The fluid management algorithms can maintain a selected intra-cavity pressure as is known in the art. In such as system, the outflow tubing 226 can be detached from the Luer connector 228 and attached to the tool 242 to provide for fluid outflows through an outflow channel 264 in the tool shaft 240 as is known in the art (see FIGS. 4B-4C).

In another aspect, referring to FIGS. 2 and 5, the design of endoscope 100 allows for the use of a sensor chip 160 having a large diagonal dimension DD relative to the cylindrical insertion profile CP of the shaft assembly 110 and working end 115 in the first position of FIGS. 1, 2 and 4A (alternatively, the diameter D of shaft 110, outer sleeve 120). At the same time, the design of the endoscope 100, when moved to the deployed profile DP and second deployed position of FIG. 4B, allows for a working channel 125 extending through the shaft 110 that has a large channel diameter WCD relative to the cylindrical insertion profile CP (diameter D of shaft 110) of FIGS. 1, 2 and 4A. In one variation, the cylindrical insertion profile CP of FIG. 4A has a diameter of 4.45 mm and the increased cross-section of the deployed profile DP of FIG. 4B is 6.23 mm.

Referring to FIGS. 4A and 5, it again can be seen that the endoscope shaft 110 has a diameter D extending about a longitudinal axis 111 to a the working end 115, a sensor chip 160 with a diagonal dimension DD carried by the sensor housing 164, and a working channel with diameter WCD extending through the shaft 110, wherein the open passageway 255 in outer sleeve 120 distal from working channel 125 of inner sleeve 122 has a lesser cross-section in the first position of FIG. 4A and a greater cross-section in the position of FIG. 4B to thus accommodate the tool 240 introduced therethrough.

In a variation, the combination of sensor chip's diagonal dimension DD and the working channel diameter WCD are greater than the cylindrical insertion profile CP (see FIGS. 4A and 5). In such a variation, the diagonal dimension DD of sensor chip 160 has a ratio of greater than 0.5:1 relative to the cylindrical insertion profile CP, or a ratio of greater than 0.6:1 relative to profile CP. In a variation, the working channel diameter WCD in the deployed profile DP has a ratio of than 0.5:1 relative to the cylindrical profile CP, or a ratio of greater than 0.6:1 relative to the cylindrical profile CP.

In one variation, the CMOS sensor chip described above (OmniVision part number OV9734 CMOS 720p HD Pur-Cel® sensor) has width and height dimensions of 2.5 mm×1.72 mm with a diagonal dimension DD of 3.06 mm. In this variation, the cylindrical insertion profile CP (or diameter D) is 4.45 mm and thus the ratio of the sensor chip diagonal DD relative to the cylindrical profile CP is 0.69:1. In this variation, the working channel diameter WCD is 3.02 mm and thus the ratio of the working channel diameter WCD in the deployed profile DP relative to the cylindrical profile CP is 0.68:1.

Referring to FIGS. 1 and 3, a control pad 270 is provided in the handle 106 with actuator buttons 272 for operating the endoscope 100, which for example can turn on/off the image sensor 160, capture still images, adjust light emitted from the LEDs, etc. In a variation, the control pad 270 can also be provided with buttons, toggles or the like to operates various aspects of the fluid management system comprising inflow pump 265 and negative pressure source 225, such as flow rates, flush, a selected set pressure and the like. Controls for the endoscope and fluid management aspects of the system can also be provided in the console B (FIG. 1) or on an independent re-usable pad that can be attached to the handle 106 of the endoscope 100 or in a connector (not shown) that couples with cable 168 extending away from the handle 106.

Figure 6:
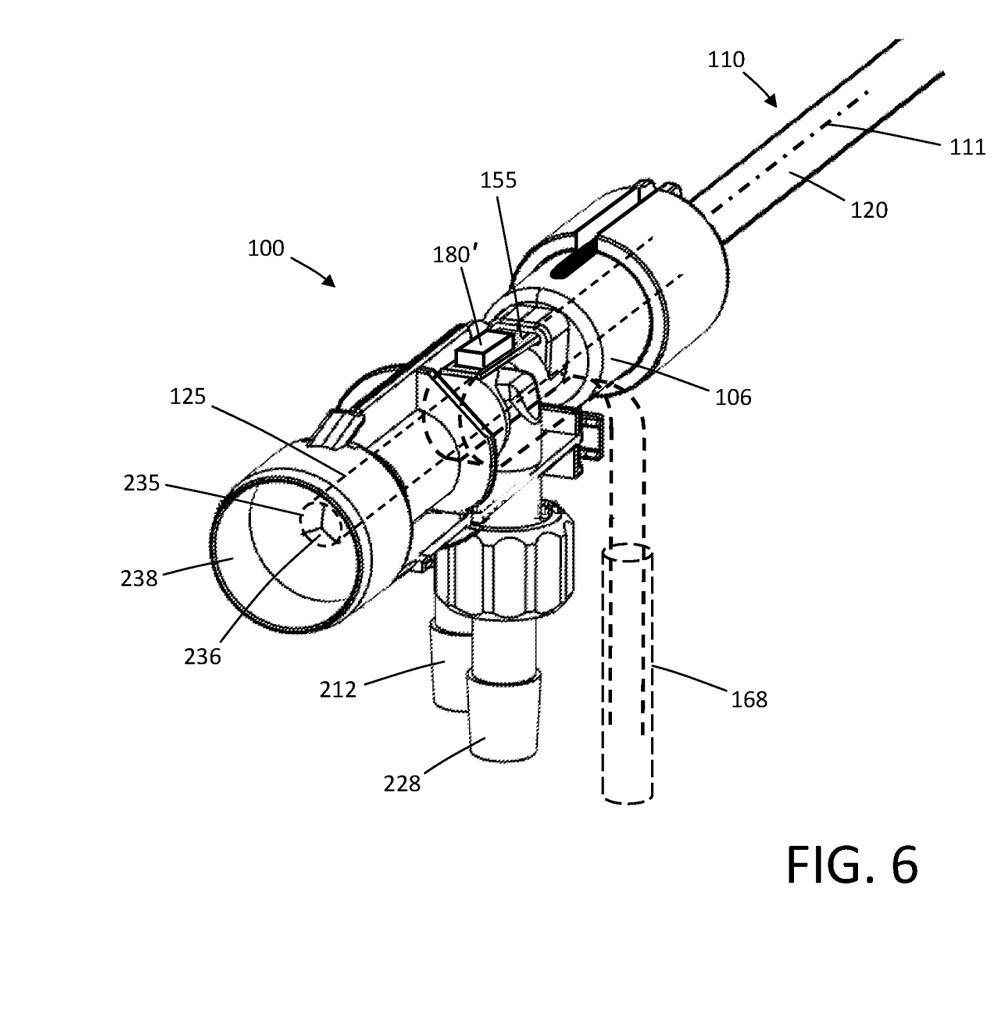
FIG. 6 is a perspective view of the endoscope of FIG. 1 from a different angle showing the proximal end of the handle and a seal at the proximal end of the working channel.

Referring now to FIG. 6, the interior core 206 of the handle 106 is shown from a different angle with the outer shell 202 of FIG. 1 removed. In this view, it can be seen that the working channel 125 extends through the handle core 206 to a proximal opening 235 a seal 236. The recess 238 in the proximal end of handle core 206 is configured for receiving the distal end of a tool and then directing the tool into the proximal opening 235 and seal into the working channel 125.

FIG. 6 also shows an optional location for an accelerometer 180' which again is coupled to a single flex circuit 155. An accelerometer 180' in this location in the handle core 206 can operate as described previously to send position signals to the image processor 170 and controller 175. In another variation, a first accelerometer 180 can be located on the flex circuit 155 proximate the image sensor 150 as shown in FIG. 2 and a second accelerometer 180' can be located on the flex circuit 155 in the handle as shown in FIG. 6. In such a variation, signals from both accelerometers 180 and 180' can be processed to confirm rotational positions or one accelerometer can be used as a backup if signals from the other accelerometer fail for any reason.

Figure 7:
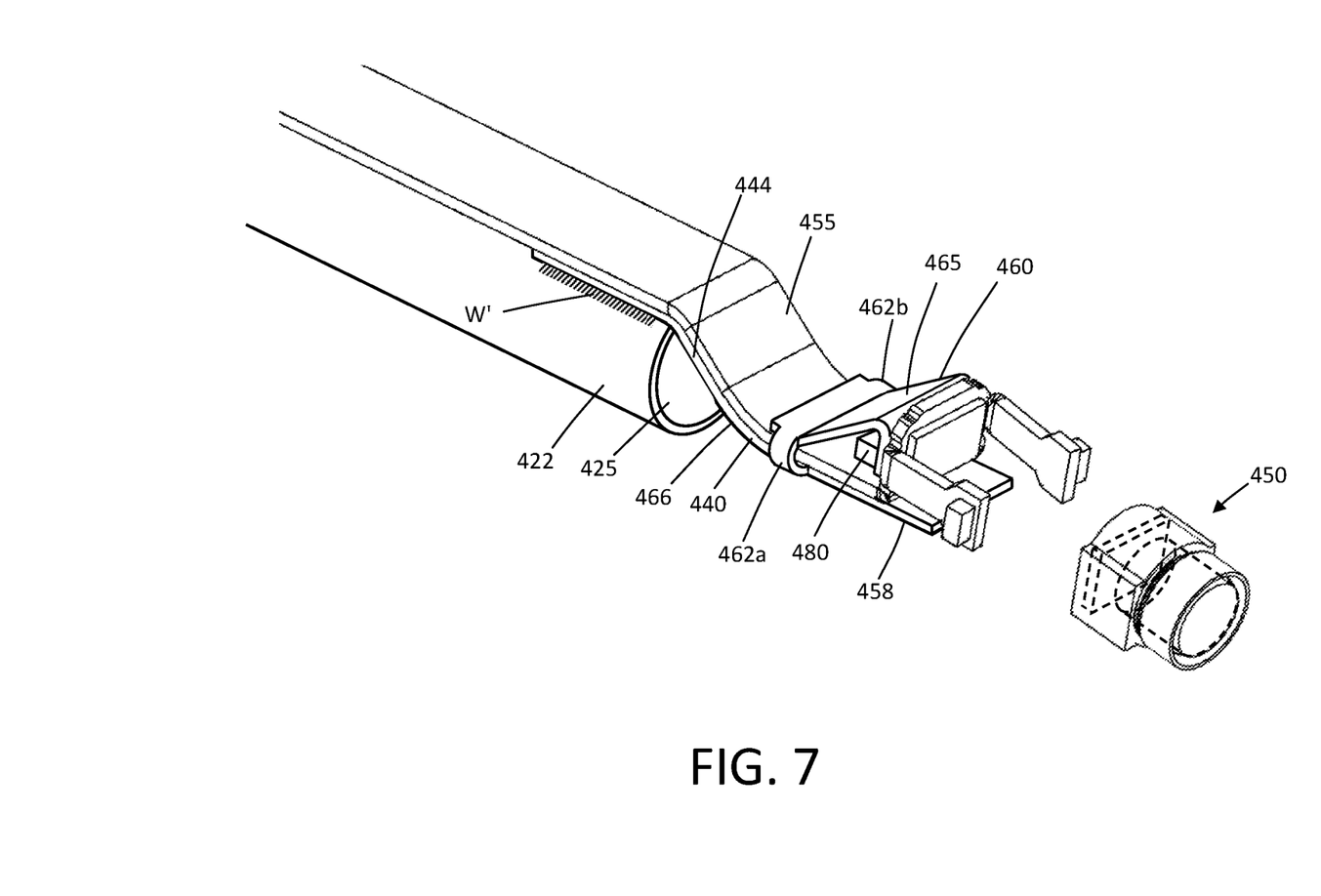
FIG. 7 is a perspective view of a portion of another variation of an endoscope similar to that of FIGS. 1 and 2 showing an inner sleeve and flexible spring structure carrying an image sensor, where the spring structure has a single living hinge.
Figure 8A:
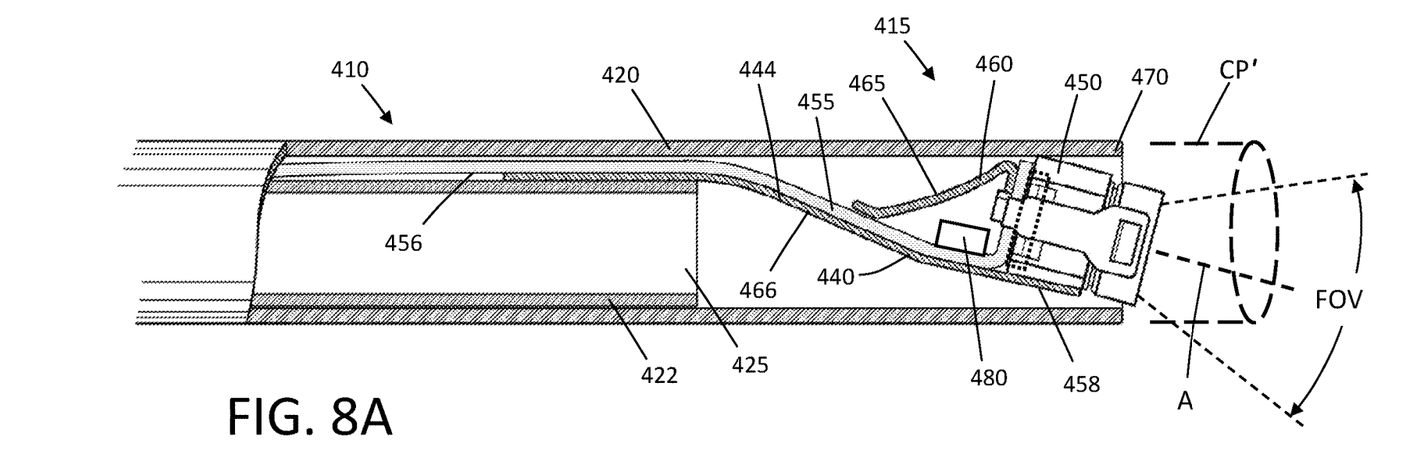
FIG. 8A is a view of a distal portion of the endoscope of FIG. 7 in a first, straight insertion configuration with an outer sleeve and inner sleeve in part-sectional views, with the flexible spring structure and image sensor constrained within the bore of the outer sleeve.
Figure 8B:
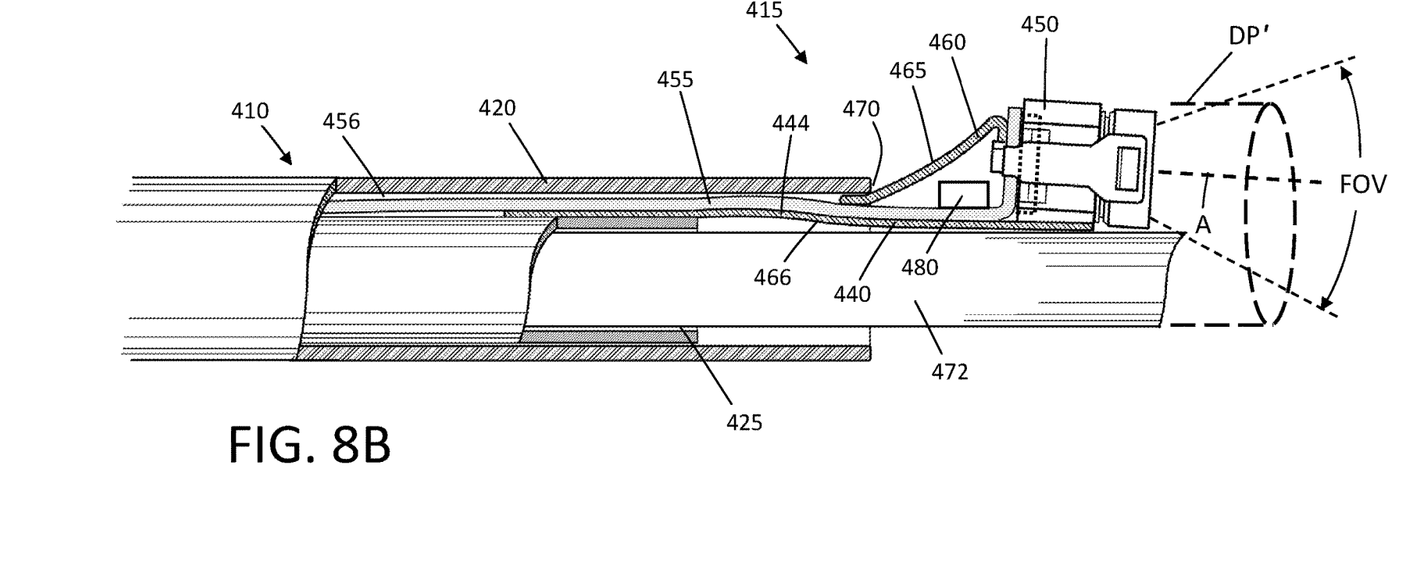
FIG. 8B is a view of the endoscope of FIG. 8A in a second deployed configuration with the outer sleeve retracted and the image sensor moved outwardly and away from the axis of the shaft by the spring force inherent in the single living hinge portion of the flexible spring structure.

Now turning to FIGS. 7, 8A and 8B, another variation of endoscope working end 415 is shown which is similar to that of FIGS. 1-6. The variation of FIGS. 7-8B again has a shaft 410 with an outer sleeve 420 and an inner sleeve 422 with working channel 425, where the outer sleeve 420 is axially moveable and configured to actuate a metal spring structure 440 between a first cylindrical insertion configuration CP' and a second deployed configuration DP' (see FIGS. 8A-8B). In this variation, the spring structure 440 is simplified and includes a single living hinge portion 444. The inner sleeve 422 is coupled with weld W' to the spring structure 440 that carries an image sensor 450 with optical axis A and field of view FOV is the same as described previously. As can be seen in FIGS. 8A and 8B, the flex circuit 455 extends through the shaft 410 in the space or inflow channel 456 between the inner and outer sleeves (420, 422). The image sensor 450 has an inferior surface that is bonded to distal end 458 of the spring structure 440. As can be seen in FIG. 7, a secondary ramp element 460 (typically metal) is connected to the spring structure 440 with lateral couplings 462a and 462b. The ramp element is adapted to provide a first or superior deflecting surface 465. The inferior surface of the spring structure 440 is configured with a second or inferior deflecting surface 466. Both the deflecting surfaces 465 and 466 may be used to actuate or move the spring structure 440 between the first position of FIG. 8A and the second position of FIG. 8B. As can be understood from FIGS. 8A and 8B, in one variation, the inner sleeve 420 can be retracted such that the distal edge 470 of outer sleeve 420 slides along superior deflecting surface 465 and the spring force inherent in a tensioned living hinge 444 can move the spring structure 440 and image sensor 450 to the second position of FIG. 8B. In another variation that can be understood from FIG. 8B, a tool 472 can be advanced through the working channel 425 such that the tool 472 will contact the inferior deflecting surface 466 of spring structure 440 and move a partially tensioned or non-tensioned living hinge 444 to the second position of FIG. 8B. In all other respects, the features of the endoscope 400 of FIGS. 7-8B operate as described previously. In this variation, an accelerometer 480 is shown coupled to the flex circuit 455 proximal to the image sensor 450.

In the variations of working ends (115, 415) described above, the spring structures (140, 440) and image sensors (150, 450) and the distal portions of flex circuits (155, 455) are illustrated in a skeletal form which is economical and suitable for an endoscope used in medical procedures. It should be appreciated that such spring structures and image sensors can be disposed within a housing or elastomeric covering, or molded into an elastomer (not shown), and fall within the scope of the invention.

In general, an endoscope of the invention comprises a handle coupled to an elongated shaft extending about a longitudinal axis to a distal end that carries a spring structure or flexible member with an image sensor at the distal end of the shaft, and where the spring structure is moveable between (i) an insertion position having a first reduced shaft profile where the field of view is oriented to observe insertion of the shaft through a body passage, and (ii) at least one deployed position having a second expanded shaft profile with the image sensor moved away from the longitudinal axis such that the field of view is oriented to observe a tool introduced through the working channel into a working space. The endoscope further includes at least one LED proximate the image sensor that is coupled to the image sensor. Additionally, an accelerometer is carried by the endoscope positioned proximal to the image sensor where the accelerometer is configured to send image signals to an image processor which includes algorithms for displaying images on a display in a selected orientation no matter what the rotational position of the shaft and image sensor may be.

In general, a method of the invention comprises providing a system including an endoscope, image processor, controller and inflow and outflow pumps, where the endoscope has an axially-extending shaft with a distal spring structure carrying an image sensor, where the spring structure is moveable between (i) a first configuration with a reduced profile where the sensor's field of view is oriented to observe introduction of the shaft through a passage in the patient's body, and (ii) at least one second configuration having an expanded profile with the image sensor moved away from the shaft axis where the field of view is oriented to observe a tool introduced through a working channel therein, and wherein the steps of the method include introducing the shaft in the first configuration through a body passageway into a working space while viewing images from the image sensor, operating the inflow and outflow pumps with the controller to circulate fluid flows within the patient's body, moving the spring structure from the first configuration to the second configuration, advancing a tool through a working channel into the working space, and viewing the tool with images from the image sensor and performing a treatment in the working space with the tool. The method includes using an accelerometer to send position signals to the controller and image processor, and then operating the controller and image processor to continuously adjust images on a display to a selected orientation, for example, an upright orientation. The method further include the step of operating the inflow and outflow pumps to circulate fluid flows while maintaining a selected pressure in the working space.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. Particular features that are presented in dependent claims can be combined and fall within the scope of the invention. The invention also encompasses embodiments as if dependent claims were alternatively written in a multiple dependent claim format with reference to other independent claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

What is claimed is:

1. An endoscopic device for use with a tool, the endoscopic device, comprising:
   an elongated shaft having an open passageway extending therethrough;
   a sensor assembly comprising an image sensor;
   an inner sleeve disposed within the open passageway;
   a flex circuit coupled to the sensor assembly and disposed within the open passageway, wherein the flex circuit comprises a flex circuit deflecting surface, wherein the flex circuit deflecting surface is configured to displace upon advancement of the tool against the flex circuit deflecting surface; and
   a flexible arm structure, wherein the flexible arm structure has a first living hinge portion and a second living hinge portion, the first living hinge portion and the second living hinge portion both having inherent spring forces, wherein the flexible arm structure has a flexible arm deflecting surface distal to the first living hinge portion, a first end coupled to the sensor assembly, and a second end within the open passageway and affixed to the inner sleeve, and wherein the flexible arm structure comprises an insertion position when restrained within the elongated shaft such that the flexible arm structure positions the sensor assembly such that an optical axis of the image sensor is angled relative to a shaft axis of the elongated shaft.

2. The endoscopic device of claim 1, wherein the flexible arm structure comprises a first leg portion and a second leg portion, wherein the first leg portion and the second leg portion extend proximally.

3. The endoscopic device of claim 2, wherein the first leg portion and the second leg portion define an opening therebetween, wherein the opening is configured to receive the flex circuit.

4. The endoscopic device of claim 2, wherein the flex circuit is configured to pass through a gap between the first leg portion and the second leg portion.

5. The endoscopic device of claim 1, wherein the elongated shaft is moveable relative to the inner sleeve, the flexible arm structure, and the sensor assembly.

6. The endoscopic device of claim 1, wherein the flexible arm structure biases towards a deployed position when unrestrained by the elongated shaft such that the flexible arm structure positions the sensor assembly away from the shaft axis of the elongated shaft.

7. The endoscopic device of claim 1, wherein as the flexible arm structure moves through the open distal end of the elongated shaft, the sensor assembly moves between the insertion position and a deployed position such that a field of view is oriented to observe the tool advanced through the open distal end of the elongated shaft.

8. The endoscopic device of claim 1, wherein the flexible arm structure is tensioned in a first position.

9. The endoscopic device of claim 1, wherein the flexible arm deflecting surface comprises an angled portion of the flexible arm structure that is non-flexible.

10. The endoscopic device of claim 1, wherein the flexible arm deflecting surface comprises a ramp portion coupled to the sensor assembly.

11. The endoscopic device of claim 1, wherein the elongated shaft is configured to contact the flexible arm deflecting surface to move the flexible arm structure between an insertion position and a deployed position.

12. The endoscopic device of claim 1, wherein further comprising a handle, wherein the flex circuit extends into the handle.

13. The endoscopic device of claim 1, wherein the inner sleeve comprises a working channel extending in the open passageway, the working channel having a wall along an interior surface of the inner sleeve such that the open passageway external to the working channel forms a fluid channel, wherein the fluid channel is coupled to the open passageway of the elongated shaft.

14. The endoscopic device of claim 13, wherein the working channel is configured to be coupled to a negative pressure source.

15. The endoscopic device of claim 1, wherein the image sensor is configured to send image signals to an image processor, wherein the image processor comprises algorithms for displaying images on a display in a selected orientation in any rotational position of the inner sleeve and the image sensor.

16. The endoscopic device of claim 1, further comprising at least a first illumination source and a second illumination source positioned at a distal end of the flex circuit.

* * * * *